(12) United States Patent
Nara et al.

(10) Patent No.: US 7,532,328 B2
(45) Date of Patent: May 12, 2009

(54) CIRCUIT-PATTERN INSPECTION APPARATUS

(75) Inventors: Yasuhiko Nara, Hitachinaka (JP);
Masaaki Nojiri, Hitachinaka (JP);
Kouichi Hayakawa, Hitachinaka (JP);
Takashi Hiroi, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 11/907,562

(22) Filed: Oct. 15, 2007

(65) Prior Publication Data

US 2008/0174772 A1    Jul. 24, 2008

Related U.S. Application Data

(63) Continuation of application No. 10/896,895, filed on Jul. 23, 2004, now Pat. No. 7,292,327.

(30) Foreign Application Priority Data

Jul. 25, 2003    (JP)    ............... 2003-201458

(51) Int. Cl.
*G01B 11/00*    (2006.01)
(52) U.S. Cl. .................. 356/394; 356/237.2
(58) Field of Classification Search ............. 356/394, 356/237.2
See application file for complete search history.

(56) References Cited

U.S. PATENT DOCUMENTS

| 4,778,745 A | 10/1988 | Leung |
| 4,806,774 A | 2/1989 | Lin et al. |
| 5,502,306 A | 3/1996 | Meisburger et al. |
| 6,040,911 A | 3/2000 | Nozaki et al. |
| 6,229,331 B1 | 5/2001 | Kuwabara |
| 6,252,981 B1 | 6/2001 | Guest et al. |
| 6,476,913 B1 | 11/2002 | Machida et al. |
| 6,509,750 B1 | 1/2003 | Talbot et al. |
| 6,759,655 B2 | 7/2004 | Nara et al. |
| 7,109,483 B2 * | 9/2006 | Nakasuji et al. ............. 250/310 |
| 7,327,871 B2 * | 2/2008 | Ishikawa ..................... 382/145 |
| 2004/0057611 A1 | 3/2004 | Lee et al. |
| 2004/0264760 A1 * | 12/2004 | Ishikawa ..................... 382/145 |

FOREIGN PATENT DOCUMENTS

| JP | 2000-161948 | 6/2000 |
| JP | 2000-162143 | 6/2000 |
| JP | 2001-156132 | 6/2001 |
| JP | 2002-048722 | 2/2002 |
| JP | 2002-228606 | 8/2002 |
| JP | 2003-083908 | 3/2003 |

OTHER PUBLICATIONS

Japanese Office Action, issued in Japanese Patent Application No. 2003-201458, dated on Jun. 5, 2007.

* cited by examiner

*Primary Examiner*—Roy Punnoose
(74) *Attorney, Agent, or Firm*—McDermott Will & Emery LLP (57) ABSTRACT

The disclosed subject matter is related to a circuit pattern inspection apparatus for detecting a gradual changing of defect expanding over a large area of the semiconductor wafer. In order to detect a gradual changing of a defect related condition expanding over a large area of the semiconductor wafer, comparison is made between dies on a wafer that are separated from each other by a distance of at least one die width. For example, when a value according to a difference between such dies exceeds a pre-determined value, an existence of the gradual changing can be confirmed.

3 Claims, 6 Drawing Sheets

CIRCUIT-PATTERN INSPECTION APPARATUS

RELATED APPLICATIONS

This application is a Continuation of U.S. application Ser. No. 10/896,895, filed Jul. 23, 2004, now U.S. Pat. No. 7,292,327, claiming priority of Japanese Application No. 2003-201458, filed Jul. 25, 2003, the entire contents of each of which are hereby incorporated by reference.

TECHNICAL FIELD

The present subject matter relates to techniques and equipment for circuit-pattern inspection, used in manufacturing of a semiconductor devices and photomasks.

BACKGROUND

In the manufacturing process of a circuit pattern formed on the semiconductor device and the photomasks, it is difficult to avoid the occurrence of a defects such as a production failure and the adhesion of foreign materials. For this reason, the following inspection apparatuses are put to practical use: an optical pattern inspection apparatus that irradiates a target to be inspected with white light, and that then compares between circuit patterns of the same kind of a plurality of LSIs by use of an optical image to extract a defect; and a SEM pattern inspection apparatus that applies the scanning electron microscope technology, and that thereby compares circuit patterns by use of an electron-beam image, the resolution of which is higher than that of the optical image, to extract a defect.

Because the inspection speed of this SEM pattern inspection apparatus is slower than that of the optical pattern inspection apparatus, the SEM pattern inspection apparatus is so devised that instead of specifying a semiconductor chip (that is to say, all dies) on a semiconductor wafer, a die to be inspected can be specified (for example, refers to Japanese Patent Laid-Open No. 2000-162143 (FIGS. 13, 14)).

Japanese Patent Laid-Open No. 2000-162143 discloses that an operator can specify dies as an area of inspection. The image comparison checking is a method in which adjacent dies are inspected and compared in sequence. The comparing between the adjacent dies makes it possible to identify a defect. A pattern inspection method of the prior art has performed by comparing between adjacent dies, in a whole semiconductor wafer or in a part of the semiconductor wafer.

SUMMARY

Although the prior art technique can identify the defect based on detecting a difference between adjacent dies, it can not detect a defect changing gradually extending over a large area of the semiconductor wafer. Although a total charge or difference across a wafer may be substantial and result in a defect, the incremental difference from one die to the next may be too small to discriminate as a defect.

An object is to provide: a circuit pattern inspection apparatus for detecting a gradual changing of defect expanding over a large area of the semiconductor wafer.

In order to detect a gradual changing of defect expanding over a large area of the semiconductor wafer, comparison is made between dies on a wafer that are separate, e.g. by one or more intervening dies or by a distance of at least on die width. And for example, when a value according to a difference between the dies exceeds a pre-determined value, an existence of the gradual changing can be confirmed.

A circuit-pattern inspection apparatus comprises: a beam system having a beam source, a detector for detecting signal obtained from beam irradiation part on a specimen, a memory for memorizing the signal as an image, and an operation unit for setting a die to be inspected on a semiconductor wafer and a die to be used as the reference die. The reference die is separated from the die to be inspected on the semiconductor wafer. A processing unit compares an image memorized in the memory of a die to be inspected with a reference image memorized in the memory of the selected reference die, and discriminates defects on the die to be inspected based on a result of the comparison the image of the die to be inspected and the reference image.

According to above subject matter, a defect changing gradually extending over a large area of the semiconductor wafer can be detected by selecting the reference die that is separated from the die to be inspected as the reference die. The defect changing gradually extending over a large area of the semiconductor wafer can be detected, because even if the changing of distribution between dies is gradual, it is emphasized by comparing between separated dies.

Furthermore the other object is to provide a circuit pattern inspection apparatus for detecting a defect which a technique comparing the die to be inspected with the reference die along an arrangement of dies as the prior art can not detect. Because the comparison technique between dies compares the die to be inspected with the reference die, if there is almost no difference between the die to be inspected with the reference die, the die to be inspected is recognized as a correct die. But the defect may be in existence in case of comparing the die to be inspected with the other reference die.

For example, in case of the reference die having a same feature as the die to be inspected according to the defect, it can not discriminate the feature as a defect. This fact means that there are defects can not be discriminated according to what order of the dies the comparison is performed and which die is set as the reference die.

In order to detect the defect can not be detected by the technique comparing the die to be inspected with the reference die along the arrangement of dies as the prior art, the comparison between the dies is performed by setting a die being separated from a die to be inspected as a reference die and an order of dies being compared.

A circuit-pattern inspection apparatus comprises: a beam source, a detector for detecting signal obtained from beam irradiation part on a specimen, a memory for memorizing the signal as an image, and an operation unit for setting a die to be inspected on a semiconductor wafer and a die to be used as the reference die and an order of comparison between the die to be inspected and the reference die. The reference die is separated from the die to be inspected on the semiconductor wafer. A processing unit compares an image memorized in the memory of a die to be inspected with a reference image memorized in the memory of the selected reference die according to the order set by the operation unit, and discriminates defects on the die to be inspected based on a result of the comparison the image of the die to be inspected and the reference image.

The further detailed composition and effects of the present subject matters are made obvious in the following description of exemplary embodiments.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION

In the following detailed description, numerous specific details are set forth by way of examples in order to provide a thorough understanding of relevant teaching. However, it should be apparent to those skilled in the art that the present teaching may be practiced without such details. In other instance, well known methods, procedures, components, and circuitry have been described at a relatively high-level, without detail, in order to avoid unnecessarily obscuring aspects of the present concepts.

Embodiments of a circuit-pattern inspection apparatus will be described in detail with reference to drawings as below. In this embodiment, targets to be inspected include a resist pattern, a CONT system's opening pattern, a Fine pattern after etching (diffusion system), and a Fine pattern after etching (wiring system). A defect on these targets is detected by comparing die images.

Figure 1:
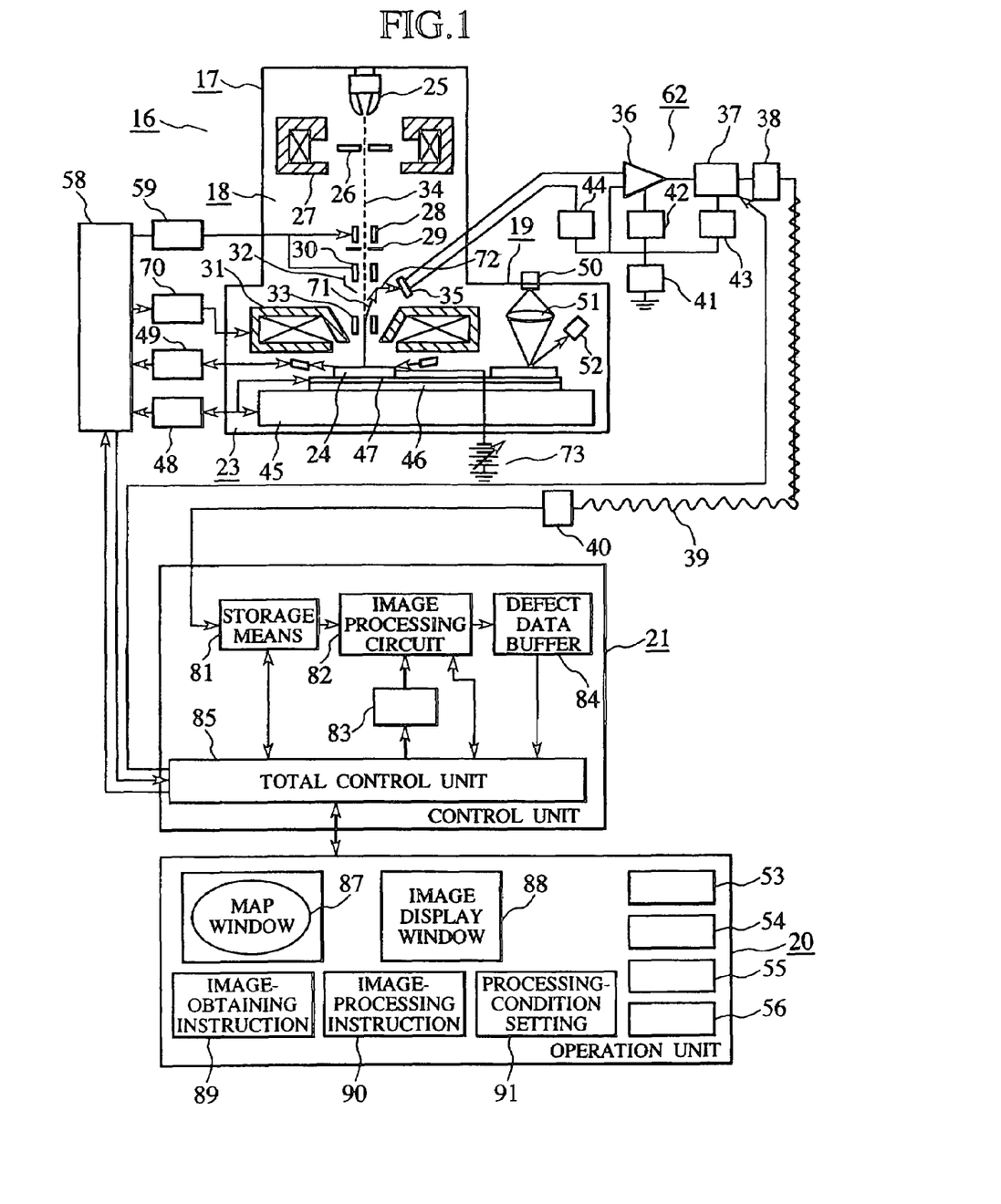
FIG. 1 is a longitudinal sectional view schematically illustrating a configuration of a circuit-pattern inspection apparatus.

FIG. 1 is a longitudinal sectional view schematically illustrating a configuration of a circuit-pattern inspection apparatus. A circuit-pattern inspection apparatus 16 comprises an inspection cabinet 17 that is vacuum pumped, and an extra cabinet (not illustrated) used to transport to the inspection chamber 17 a substrate to be inspected 24. This extra cabinet is devised to be capable of being vacuum-pumped independently of the inspection chamber 17. Incidentally, the reason why the circuit-pattern inspection apparatus 16 is configured in such a manner is because an electron beam is used. Therefore, in the case of a laser beam, or the like, it is not necessary to adopt a vacuum-pump structure. In addition, the circuit-pattern inspection apparatus 16 includes not only the inspection chamber 17 and the extra cabinet, but also a control unit 21 and an operation unit 20.

Broadly classifying, the inspection chamber 17 comprises an electro-optic system 18, a secondary electron detector part 62, a target chamber 23, and an optical microscope 19. The electro-optic system 18 comprises an electron gun 25, an electron-beam emitting electrode 26, a condensing lens 27, a blanking deflector 28, an iris 29, a scanning deflector 30, an objective lens 31, a reflector plate 32, and an ExB deflector 33. The electro-optic system 18 forms an irradiation means.

Applying the voltage to a point between the electron gun 25 and the electron-beam emitting electrode 26 causes the electron gun 25 to emit a primary electron beam 34. Acceleration of the primary electron beam 34 is achieved by applying the high-voltage electronegative potential to the electron gun 25. The primary electron beam 34 travels in the direction of the substrate to be inspected 24 by the energy equivalent to the potential, and is then converged by the condensing lens 27. Further, the primary electron beam 34 is thinly narrowed by the objective lens 31 before the substrate to be inspected 24 is irradiated with the primary electron beam 34. The substrate to be inspected 24 is a substrate having a minute circuit pattern, or the like. The substrate to be inspected 24 includes, for example, a semiconductor wafer, a chip (or a liquid crystal), and a mask. It is to be noted that a scanning signal generator 59 for generating a scanning signal and a blanking signal is connected to both the blanking deflector 28 and the scanning deflector 30, and that each of the condensing lens 27 and the objective lens 31 is provided with a lens power supply.

A correction control circuit 58 monitors the discrepancy in position and height by use of signals from a position-monitor length measuring machine 48 and from an inspected-substrate height measuring machine 49, and then generates a correction signal from its result. After that, the correction control circuit 58 transmits the correction signal to an objective-lens power supply 70 and the scanning signal generator 59 so that a correct position is always irradiated with the primary electron beam 34.

An image of a surface of the substrate to be inspected 24 is first obtained by irradiating the substrate to be inspected 24 with the thinly narrowed primary electron beam 34 to generate a secondary electron 71, and then by detecting the secondary electrons 71 in synchronization with scanning of the primary electron beam 34 and moves of an X stage 47 and of a Y stage 46.

As for the secondary electron detector part 62, the secondary electron detector 35 is placed above the objective lens 31 in the inspection cabinet 17. An output signal of the secondary electron detector 35 is amplified by a preamplifier 36 that is placed outside the inspection cabinet 17. Then, an A/D converter 37 converts the output signal into digital data. The target chamber 23 comprises a target stage 45, the X stage 47, the Y stage 46, the position-monitor length measuring machine 48, and the inspected-substrate height measuring machine 49. In addition, with the object of fine tuning the rotation of the substrate to be inspected 24, a rotatable stage (not illustrated) may also be placed on the X stage 47.

The optical microscope 19 comprises a light source 50, an optical lens 51, and a CCD camera 52. The optical microscope 19 is placed at a position that is in proximity to the electro-optic system 18 inside the inspection cabinet 17, and that is separated from the electro-optic system 18 to such an extent that the optical microscope 19 and the electro-optic system 18 do not exert an influence on each other. The distance between the electro-optic system 18 and the optical microscope 19 is made known so as to ensure the compatibility of coordinates on the substrate to be inspected 24 between the electro-optic system 18 and the optical microscope 19. The CCD camera 52 detects reflected beam from the substrate to be inspected 24. An image can be formed by output data from the CCD camera 52.

The X stage 47 or the Y stage 46 permits a substrate to be inspected 24 to reciprocate a known distance between the electro-optic system 18 and the optical microscope 19. Moreover, it may also be so devised that an angle at which the substrate to be inspected 24 is irradiated with the primary electron beam 34 can be changed by tilting an arbitrary side of a rotatable stage (not illustrated) or an arbitrary side of a target stage (not illustrated) on which the substrate to be inspected 24 is placed.

The control unit 21 comprises the following: a total control unit 85; a storage means 81 for storing a signal from the secondary electron detector part 62; an image processing circuit 82 for processing the stored digital signal; an inspection-condition setting unit 83 for setting processing parameters of the image processing circuit 82; and a defect data buffer 84 for storing defect information that is obtained as a result of the processing of the image processing circuit 82.

Figure 2:
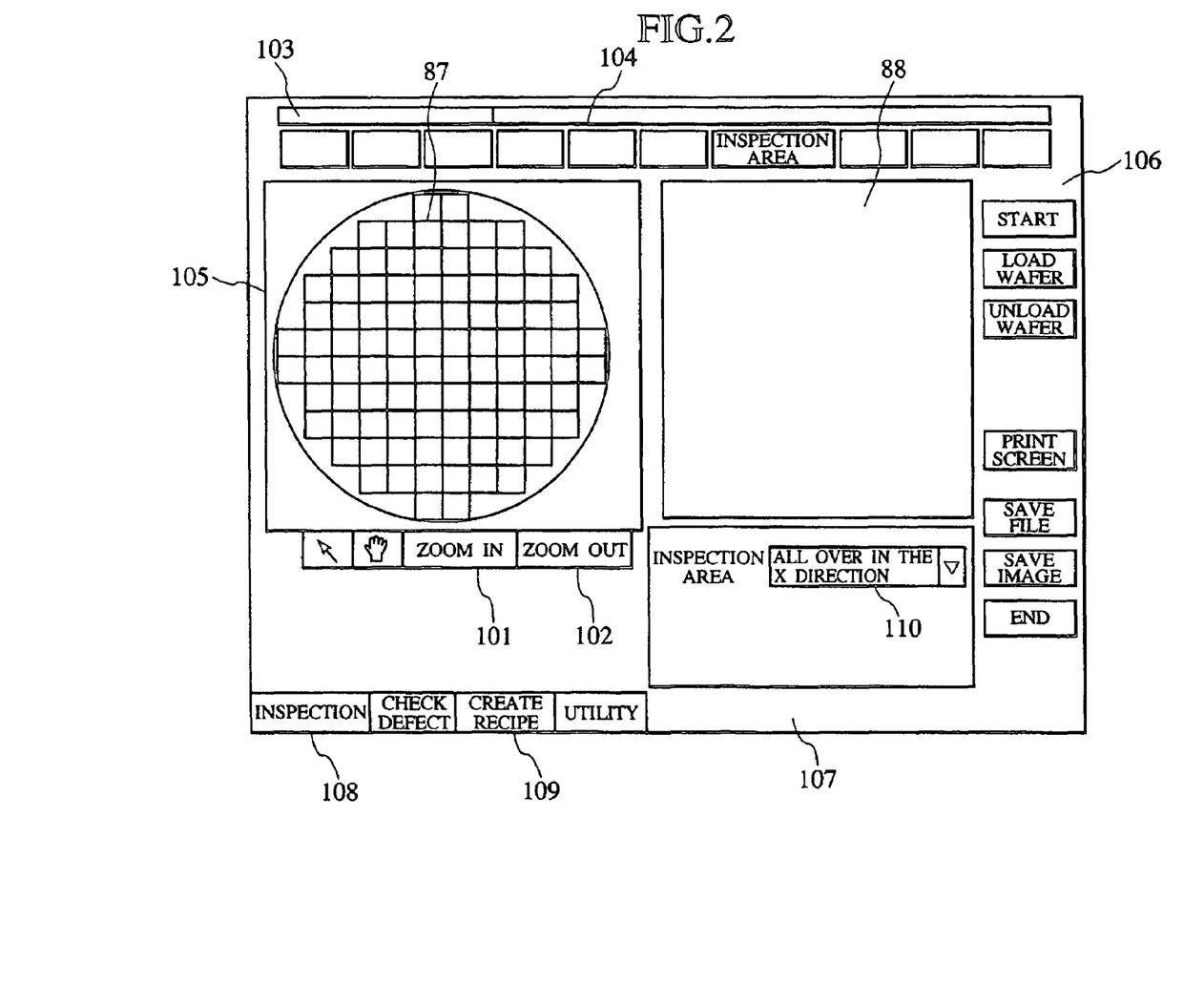
FIG. 2 is a diagram illustrating a screen configuration of an operation unit.

The operation unit 20 is provided with a display screen for displaying an image obtained, and for displaying tools for various instructions relating to inspection. The operation unit 20 also includes the following: a first stored-image display button 53 and a second stored-image display button 54, each of which is a tool for causing the operation unit 20 to display an image stored in the storage means 81. A comparison-result display button 55 causes the operation unit 20 to display the result of image comparison to extract a defect; and defect display button 56 causes the operation unit 20 to display a defect image. According to these instructions, a selected electron-beam image, a defect image, and the like, are displayed in an image display window 88 on the display screen. Further, the operation unit 20 displays a map window 87 used when giving an instruction to display a position of an inspection area on the substrate to be inspected 24, and an instruction to set an inspection area. Below the map window 87 and the image display window 88, the following are provided: an image-obtaining instruction button 89 used to give an image obtaining instruction; an image-processing instruction button 90 used when adjusting image processing, for example, the contrast of an obtained image; and a processing-condition setting button 91 used to set various kinds of conditions such as electronic optical conditions, stage control conditions, and vacuum pumping conditions. In addition, although it is not illustrated, a mode switching unit for switching a mode according to contents of operation including an inspection mode and a recipe mode may also be provided.

Figure 4:
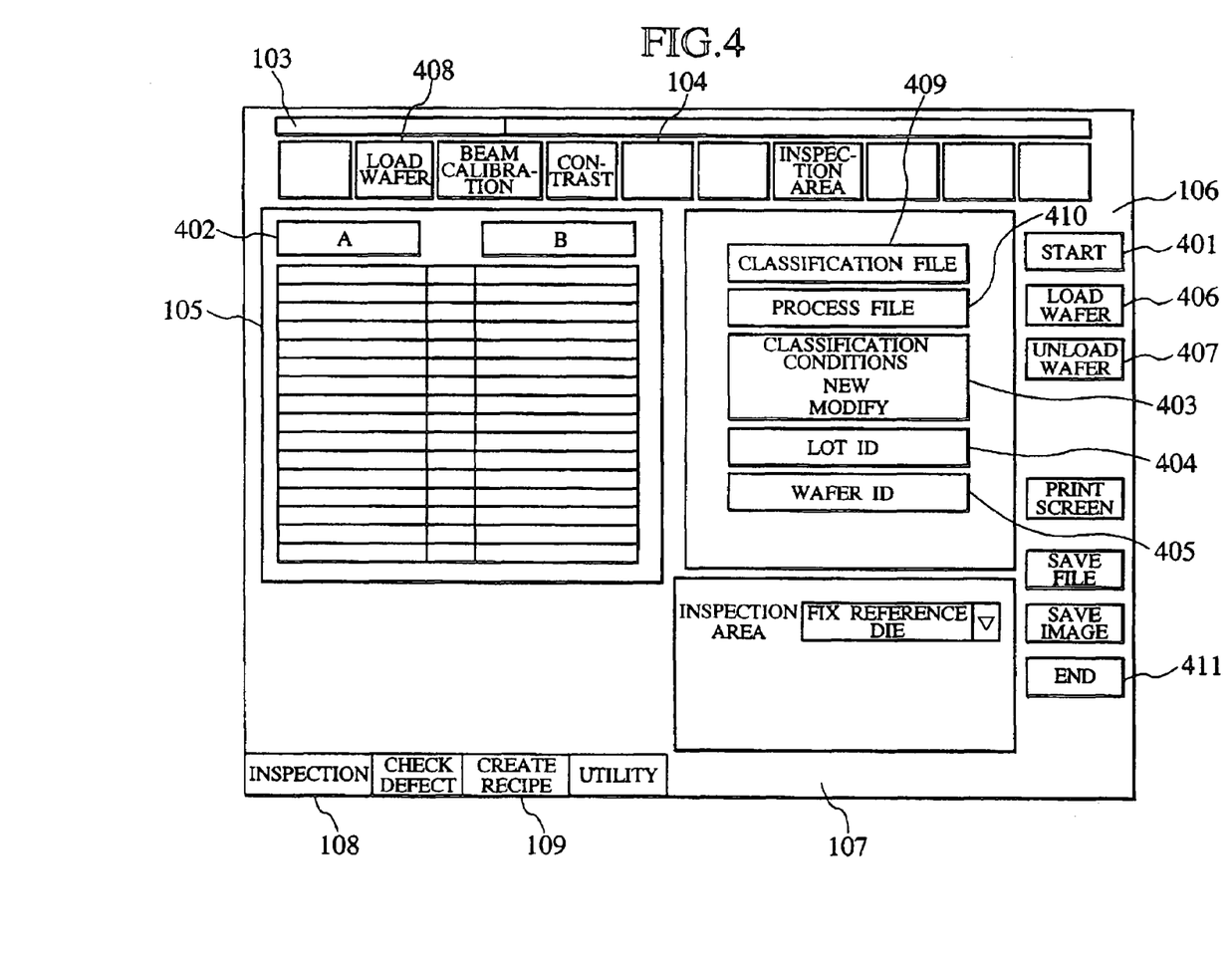
FIG. 4 is a diagram illustrating a screen used in a recipe creation mode.
Figure 5:
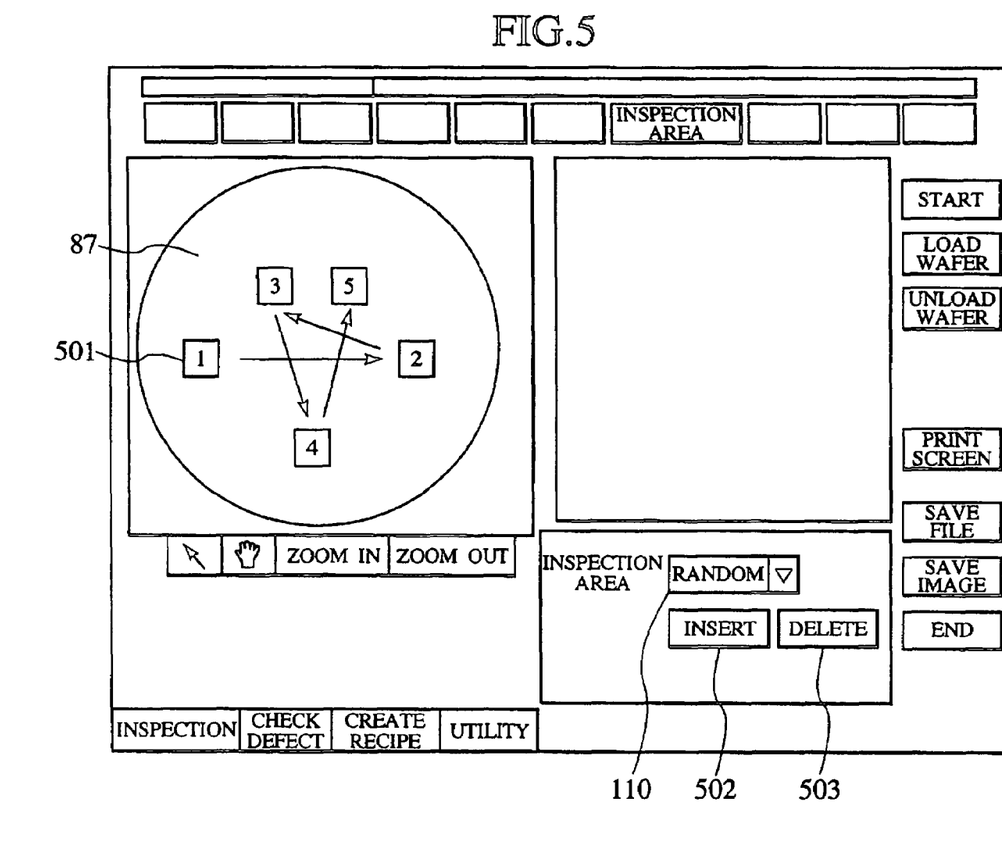
FIG. 5 is a diagram illustrating a screen for setting the inspection order of dies.
Figure 6:
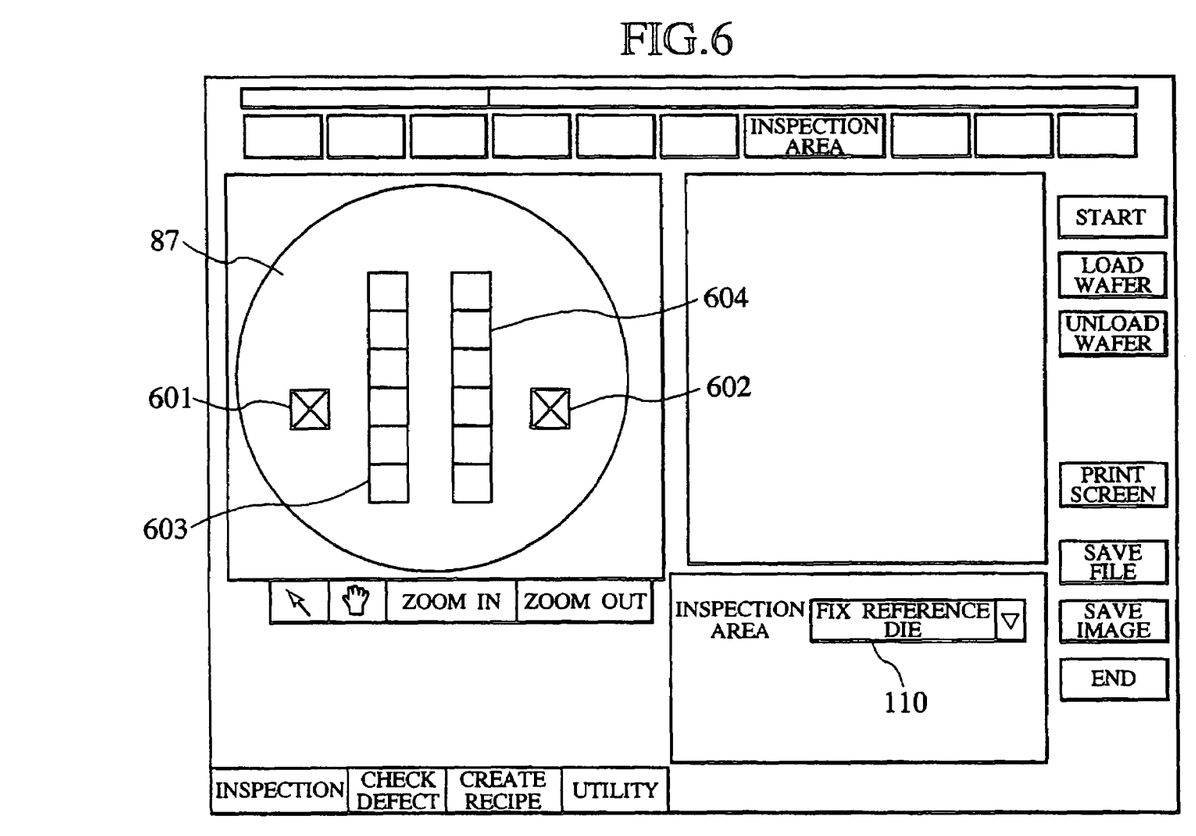
FIG. 6 is a diagram illustrating a screen used for fixed settings of a reference die.

In this specification, although these buttons illustrated in FIG. 2 and the other buttons illustrated in FIG. 4, FIG. 5, and FIG. 6 are explained as Graphical User Interface (GUI) on the display, for example, it is possible to provide a plurality of switches on the control unit 21 instead of the GUI.

Operation commands, and operating conditions, of each part of the circuit-pattern inspection apparatus 16 are inputted and output from the operation unit 20. Various conditions are inputted beforehand into the operation unit 20 so that these conditions can be set according to an object. Here, the conditions include an acceleration voltage at the time of the generation of an electron beam; the deflection width of the electron beam; the deflection speed; the signal capturing timing of the secondary electron detector part; and the moving speed of the stage.

In a manufacturing process for forming semiconductor devices in a semiconductor wafer, finding a defect and studying its cause early, and then taking early measures against the cause, will lead to an improvement in production yield. Therefore, at the time of the automatic inspection to detect a defect of a circuit pattern on the semiconductor wafer, high inspection speed is indispensable for circuit-pattern inspection apparatuses. As for the inspection apparatus using an electron beam as described in this embodiment, scanning at a low speed an electron beam having an electron-beam electric current of the order of pA, or scanning such an electron beam many times, or superimposing images on each other, as is performed with the usual SEM, results in very low inspection speed. Moreover, with the object of avoiding electrification of an insulating material, the number of times an electron beam is scanned should be once, or several times, at a high speed.

The circuit-pattern inspection apparatus in this embodiment, therefore, is so devised that an image is formed by scanning only once an electron beam having for example an electric current of 100 nA which is about one hundred times larger than that of the usual SEM. This is based on the assumptions that the scan width is 100 μm and one pixel is equivalent to 0.1 μm$^2$, and that a period of time during which scanning is performed once is 1 μs.

Incidentally, a thermal field emission electron source of a diffusion supply type is used as the electron gun 25. Because using this electron gun 25 makes it possible to ensure a stable electron-beam electric current as compared with the conventional tungsten (W) filament electron source and the cold field emission electron source, an electron-beam image with little fluctuations in brightness can be obtained. Additionally, because this electron gun 25 allows an electron-beam electric current to be set at a large value, high-speed inspection can be achieved.

A retarding power supply 73 applies a negative voltage to the substrate to be inspected 24. Depending on the structure, and a material, of a circuit pattern formed on the substrate to be inspected, there is a case where it is desirable to change the energy of the primary electron beam 34. By adjusting the voltage of the retarding power supply 73, it is possible to reduce the speed of the primary electron beam 34, and thereby to adjust the electron-beam irradiation energy applied to the substrate to be inspected 24 to an optimum value without changing the potential of the electron gun 25. The secondary electron 71, which has been emitted by irradiating the substrate to be inspected 24 with the primary electron beam 34, is accelerated by a negative voltage applied to the substrate to be inspected 24.

An ExB deflector 33 is placed above the substrate to be inspected 24. The secondary electron 71 accelerated by this ExB deflector 33 is deflected in a given direction. The amount of the deflection can be adjusted by the voltage applied to the ExB deflector 33 and the intensity of a magnetic field. In addition, this electromagnetic field can be changed in conjunction with the negative retarding voltage applied to the substrate to be inspected 24. The secondary electron 71 deflected by the ExB deflector 33 collides with the reflector plate 32 under given conditions. This reflector plate 32 has such a shape that a shield pipe and a cone are united with each other in the scanning deflector 30 used for the primary electron beam 34 with which the substrate to be inspected 24 is irradiated. When the accelerated secondary electron 71 collides with this reflector plate 32, a second secondary electron 72 having the energy ranging from several eV to 50 eV is generated from the reflector plate 32.

As described above, the secondary electron 71, which has been generated while the substrate to be inspected 24 is irradiated with the primary electron beam 34, is accelerated and then collides with the reflector plate 32, with the result that the second secondary electron 72 is generated. The secondary electron detector 35 is devised to detect the second secondary electron 72 in conjunction with the timing of scanning the primary electron beam 34.

The secondary electron detector 35, the preamplifier 36, the A/D converter 37, a preamplifier driving power supply 42, an A/D converter driving power supply 43, and a reverse bias power supply 44, are floating in a positive potential by a high voltage power supply 41. The second secondary electron 72, which has been generated as a result of the collision with the reflector plate 32, is introduced into the secondary electron detector 35 by an absorption electric field generated by a positive potential.

In the secondary electron detector part 62, a detection signal coming from the secondary electron detector 35 placed in the vacuum-pumped inspection cabinet 17 is transmitted to the preamplifier 36 placed outside the inspection cabinet 17, and then the detection signal is amplified. The A/D converter 37 converts the amplified detection signal into digital data. The A/D converter 37 is devised to immediately convert the analog signal, which has been detected by the secondary electron detector 35 and then has been amplified by the preamplifier 36, into a digital signal, and then to transmit the digital signal to the control unit 21. The detected analog signal is first digitized immediately after the detection, and then the digital signal is transmitted. Accordingly, it is possible to obtain a high-speed signal with a high SN ratio.

When performing inspection, the X stage 47 and the Y stage 46 are made stand still, and then the primary electron beam 34 is two dimensionally scanned on the substrate to be inspected 24. In another way, while the X stage 47 or the Y stage 46 is continuously moved at a constant speed, the primary electron beam 34 is scanned in an approximately right-angle direction. If a specific, relatively small area is inspected, the former inspection method in which inspection is performed with the stages being made stand still is effective; and if a relatively wide area is inspected, the inspection method in which inspection is performed while the stage is continuously moved at a constant speed is effective.

In order not to irradiate the substrate to be inspected 24 with the primary electron beam 34, instead of the scanning deflector 30, the blanking deflector 28 is used for the deflection, and the iris 29 is used for the shielding. This enables not only alternating scanning but also one-way scanning when scanning the primary electron beam 34, which makes it possible to control the degree to which the substrate to be inspected 24 is irradiated with an electron beam.

With the object of knowing where the primary electron beam 34 is applied, it is important to perform position measurement when the X stage 47 and the Y stage 46 move. In this embodiment, a length measuring machine by means of laser interferometry is used as the position-monitor length measuring machine 48. Positions of the X stage 47 and of the Y stage 46 can be monitored in real time, and its information is transmitted to the control unit 21. Moreover, other than the position-monitor length measuring machine 48, the circuit-pattern inspection apparatus 16 is so devised that data including the number of revolutions of a motor for driving the X stage 47 and the Y stage 46 is also measured and then the data is transmitted from a driver of the motor to the control unit 21. The control unit 21 can accurately keep track of an area where the primary electron beam 34 is applied, and its position according to the data. If there is a discrepancy in position at which the primary electron beam 34 is applied, position correction data is transmitted from the control unit 21 to the correction control circuit 58, and a corrected deflection signal is transmitted to the scanning signal generator 59. This makes it possible to correct the discrepancy in position in real time.

As the inspected-substrate height measuring machine 49, an optical measuring instrument which adopts a measuring method other than that using an electron beam is used; for example, a laser-interferometry measuring instrument, or a reflected-light type measuring instrument which measures a change by a position of reflected light, is used. The inspected-substrate height measuring machine 49 is devised to measure a height of the substrate to be inspected 24 placed on the X stage 47 and the Y stage 46 in real time. In this embodiment, the following method is used: irradiating the substrate to be inspected 24 with narrow white light, which has passed through a slit, over a transparent window; detecting a position of its reflected light by a position detection monitor; and calculating the amount of change in height from fluctuations in position.

On the basis of the measured data of this inspected-substrate height measuring machine 49, the focal length of the objective lens 31 used to thinly narrow the primary electron beam 34 is dynamically corrected, which makes it possible to emit the primary electron beam 34 that is always focused on a noninspection area. In addition, a warp, the height, and the distortion, of the substrate to be inspected 24 are measured in advance before irradiating with an electron beam. Therefore, on the basis of such data, it is also possible to set correction conditions for each inspection area of the objective lens 31.

An image signal of the substrate to be inspected 24, which has been detected by the secondary electron detector 35, is amplified by the preamplifier 36, and is then digitized by the A/D converter 37. After that, the digital image signal is converted into a light signal by an optical conversion means 38, and is then transmitted by an optical transmission means 39. The light signal is converted into an electric signal again by an electric conversion means 40 before the electric signal is stored in a storage means 81 of the control unit 21.

The defect detection is performed by comparing the first image signal stored in the storage means 81 with the second image signal to extract the difference between both of the image signals. The image processing circuit 82 performs various kinds of image processing with the object of aligning the first image signal with the second image signal, standardizing a signal level, and eliminating a noise signal. Then, comparison operation of both image signals is performed. An absolute value of a difference image signal resulting from the comparison operation is compared with a given threshold value on a pixel basis. If a signal level of the difference image signal is larger than the given threshold value, this pixel is judged to represent a defect candidate, and accordingly the image signal, position data, and the like, are stored in the defect data buffer 84. The image processing circuit 82 also can calculate a correlative value between the first image signal and the second image signal.

Next, condition settings at the time of inspection will be described. On a screen of the operation unit 20, the map window 87 for displaying a position of a current stage and the image display window 88 for displaying an image of the optical microscope 19 are displayed. Clicking on this map window 87 will move the X stage 47 and the Y stage 46 so that a position at which conditions are set can be selected. In addition, clicking on the image-obtaining instruction button 89 of the operation unit 20 causes the secondary electron detector part 62 to detect the secondary electron 71 or the second secondary electron 72, which is generated by irradiating the substrate to be inspected 24 with the primary electron beam 34. After that, the detected electron is converted into a digital signal, and a digital image of a given area is then stored in the storage means 81.

By clicking on the processing-condition setting button 91 of the operation unit 20, image processing conditions are set. By clicking on the image-processing instruction button 90, image processing is executed under the set processing conditions. Further, on the basis of the conditions set by the inspection-condition setting unit 83 of the control unit 21, the digital image stored in the storage means 81 is processed by the image processing circuit 82 to extract a defect, and coordinate data of the defect and an image of the defect are stored in the defect data buffer 84.

FIG. 2 is a diagram illustrating a screen configuration of the operation unit 20. FIG. 2 illustrates the operation unit 20 shown in FIG. 1 in detail. In the map window 87 of FIG. 2, an area where an image has been obtained to set inspection conditions is displayed in a manner that this area can be distinguished from the others. Clicking on the area and then pressing a zoom in button 101 will enlarge the area. By clicking on a symbolized defect in the enlarged area displayed in the map window 87, an image of the area including the defect is displayed in the image display window 88.

The above-mentioned work is repeated to search for inspection conditions that are suitable for the inspection. When the condition check at one position is completed, the map window 87 is displayed on a reduced scale again by pressing a zoom out button 102. Next, the image display window 88 is switched to an optical microscope image, and a condition-setting position is selected again. Then, the steps from the obtaining of an image to the condition settings are repeated.

Next, various kinds of parameters required to execute an inspection will be described. Such parameters include parameters that are specific to a substrate to be inspected, and parameters that determine operating conditions of an apparatus.

The parameters which are specific to a substrate to be inspected can be roughly grouped into two kinds. One is a parameter called a "classification file", which is not changed by a layer in the middle of a manufacturing process. This kind of parameter includes, for example, the size of the substrate to be inspected 24; a shape of an orientation flat or of a notch; the exposure shot size of a semiconductor product; the chip (or die) size; a memory cell area; and the iteration unit size of the memory cell. These parameters are stored in a table as a "classification file".

The other is a parameter called a "process file", which needs adjustment because a state of a surface material and a state of a surface shape differ depending on a layer in the middle of the manufacture process. This kind of parameter includes, for example, electron-beam irradiation conditions; various kinds of gains in the detection system; and image-processing conditions for detecting a defect. These parameters are written as the "process file".

At the time of inspection, by specifying the "classification file" and the "process file", it is possible to call inspection conditions corresponding to a specific semiconductor product and a specific manufacturing process. In this embodiment, the "classification file" and the "process file" are designated as a "recipe" as a whole. In addition, a series of operations relating to inputting, and writing, of these various kinds of parameters is called "recipe creation".

A recipe creation method, and an operation screen used to execute the recipe creation method, will be described as below. The recipe creation screen shown in FIG. 2 is roughly divided into five areas. An area 103 is located in the upper part of the screen. Information displayed in the area 103 includes an apparatus name, and an apparatus ID, and a classification file name and a process file name, both of which are used as a recipe name. In an area 104, guidance for describing the operation and the states is displayed. In an area 105 located in the center of the screen, displayed contents change in response to the operation and a progress state. In the example of FIG. 2, the map window 87 and the image display window 88 are displayed. In an area 106 located on the right side of the screen, operation buttons which are required for a plurality of screens in common are displayed. As examples of the operation buttons, there are "Start", "Load wafer", "Unload wafer", "Print screen", "Save file", "Save image", "End", and the like. For example, pressing the save file button will display a screen that is used to specify names of a classification file and of a process file into which a recipe currently being created is saved. In addition, pressing the save image button will display a screen used to specify a name that is required to save as an image file an image currently being displayed.

A mode name is displayed in an operation area 107 in the lower part of the screen. For example, pressing the inspection button 108 will enter an inspection mode for executing automatic inspection; and pressing the create recipe button 109 will enter a recipe creation mode for setting inspection conditions such as inputting of the above-mentioned parameters.

Incidentally, even in the case of another apparatus, a model of which is the same as that of the apparatus currently being used, creating a recipe once suffices so long as the same recipe can be used, which makes the apparatus convenient to use. Usually, a recipe cannot be transmitted to another apparatus. The inspection result, however, can be inputted into any apparatus. A defect information file which is the inspection result includes inspection conditions. Therefore, inputting the defect information file into another apparatus eliminates the need for newly creating inspection conditions from the beginning, which makes the apparatus convenient to use. If in the inspection conditions there is a condition that should be changed, it is possible to change the condition in the recipe creation mode described below.

Figure 3:
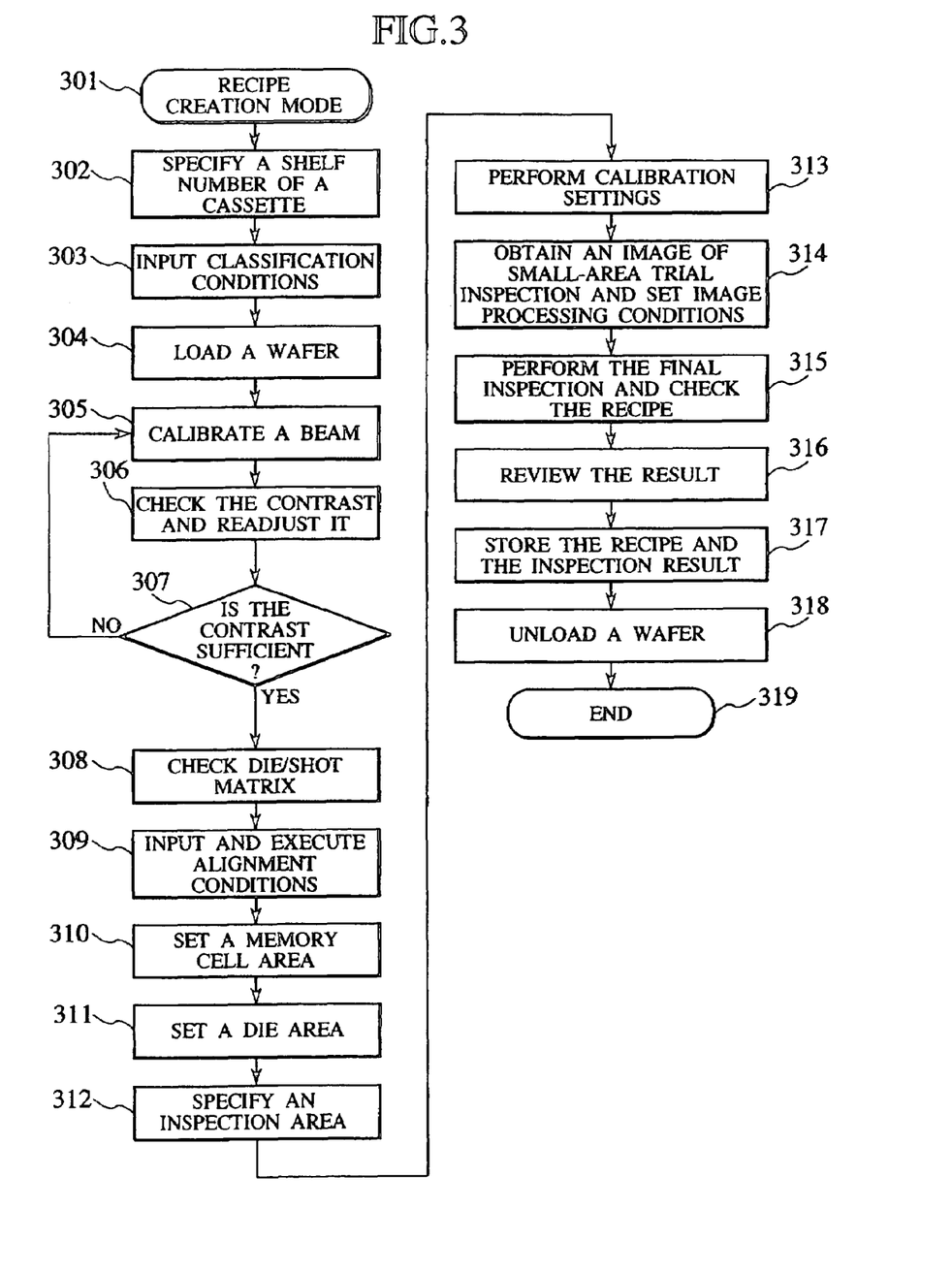
FIG. 3 is a flowchart illustrating processing of a recipe creation mode.

FIG. 3 is a flowchart illustrating processing of the recipe creation mode. Additionally, FIG. 4 is a diagram illustrating a screen used in the recipe creation mode. In the screen shown in FIG. 2, when pressing the create recipe button 109, the screen of the operation unit 20 shown in FIG. 1 is switched to a screen shown in FIG. 4, which is displayed at the time of recipe creation. A start button 401 is pressed in this screen (step 301 in FIG. 3). Next, a shelf number of a cassette in which a substrate to be inspected is stored (the shelf number is displayed in a shelf-number display area 402) is specified to call a recipe file (step 302). Then, in a classification condition entry area 403, whether classification conditions are newly created or modified is specified; in a lot ID input area 404, a lot ID is inputted; and in a wafer ID input area 405, an ID of the substrate to be inspected is inputted (step 303). When changing a classification condition, regardless of whether or not the substrate to be inspected is loaded into the apparatus, it is possible to change a recipe creation condition. The change is usually made with the substrate to be inspected being loaded.

Next, by pressing the load wafer button 406, the substrate to be inspected is loaded from the cassette to the inspection apparatus (step 304). The inspection apparatus detects the orientation flat, or the notch, of the substrate to be inspected. After that, the inspection apparatus uses a target-wafer holder to hold the substrate to be inspected in a target-wafer exchanging chamber, and then transfers the target-wafer holder to a stage of an inspection cabinet. Further, on the screen shown in FIG. 4, a message 408 indicating that a wafer is being loaded is displayed with a color different from the others.

Next, the inspection apparatus performs calibration of a beam (step 305). Calibration conditions require calibration on the basis of default recipe-file conditions stored beforehand. Accordingly, the inspection apparatus performs correction required for this substrate to be inspected, and then stores the changed conditions. The calibration conditions include irradiation conditions of the primary electron beam; the amount of correction of deflection; the amount of correction of reference coordinates; and the amount of correction of a focus parameter.

Next, the image contrast is checked by irradiating a specified position of the substrate to be inspected with the primary electron beam, and then a focus and astigmatism are readjusted (step 306). As shown in FIG. 2, an image is displayed in the image display window 88 of the area 105 in the center of the screen. If the sufficient contrast cannot be obtained (step 307), the process returns to the previous step to change the electron-beam irradiation conditions (step 305). Here, the specified irradiation conditions, and the focus and astigmatism conditions, are stored in a process file as recipe parameters.

After the irradiation conditions of the primary electron beam have been determined and the contrast has been checked, die/shot matrix are checked (step 308). To begin with, the size, and a matrix (array), of a shot of the substrate to be inspected, and the size, and a matrix (array), of a die (chip) in the shot are inputted. Next, whether or not there is a shot or a die around the perimeter of the substrate to be inspected is specified. The matrices of the shot and of the die are stored as parameters in the recipe file.

Next, alignment conditions are inputted, and thereby the alignment is executed (step 309). In more detail, the alignment includes the following steps: (1) specifying a plurality of alignment chips; (2) moving to the starting point of a first chip; (3) switching to an optical microscope monitor; (4) manually moving to an alignment mark position of the first chip; (5) writing an optical image; (6) switching to a SEM image mode; (7) manually making a fine adjustment to an alignment mark position; (8) writing a SEM image; and (9) writing alignment coordinates.

In more detail, the execution of the alignment includes the following: (1) move of a first point; (2) input of an image, search, and matching; (3) move of a second point; (4) input of an image, search, and matching; (5) move to a remaining point, search, and matching; and (6) correction of inclination, correction of a position, and correction of a chip interval.

Further, in more detail, the offset settings of the starting point of the chip include the following: (1) moving to a last point alignment mark; (2) specifying an alignment mark position (SEM image mode); (3) moving to the starting point of a first point chip; (4) specifying a position of the starting point of the chip (SEM image mode); and (5) calculating and writing an offset between the starting point and the alignment mark. The offset of the starting point of the chip is the distance from the alignment coordinates to starting point coordinates of the chip including the mark.

Thus, a value of the offset from specified pattern coordinates for alignment to the starting point of the chip is inputted, and this offset value is then written into the process file as an alignment parameter. As for the recipe creation, there are many parameters for specifying coordinates used to execute various kinds of processing on a wafer. Accordingly, the alignment conditions are first determined and written, and then processing up to the alignment is executed.

Next, a memory cell area in the chip is set (step 310). In more detail, the memory cell area settings include the following: (1) inputting a cell area; (2) inputting the cell pitch; and (3) memorizing (1) and (2) to the storage means 81. The cell area is inputted by use of an optical-microscope image and an electron-beam image.

Next, a die area is set (step 311). In more detail, the die area settings include the following: (1) inputting a die area; (2) inputting a die noninspection area; and (3) memorizing (1) and (2) to the storage means 81. The die area is also inputted by use of an optical-microscope image and an electron-beam image.

Next, an inspection area is specified (step 312). When specifying the inspection area, two kinds of inspection areas can be specified, one is an inspection die and another is an inspection area in the die. If it is not necessary to inspect all dies, or if only a specific area in a die needs to be inspected, it is possible to specify it arbitrarily. Moreover, with the object of further specifying, in the specified area, an inspection area or an area that needs not be inspected, it is also possible to specify an inspection sampling rate and a skipping method.

Additionally, it is also possible to specify inspection in the X direction, or inspection in the Y direction. Data as to the die area and the inspection area are stored as parameters in the process file.

As described later, the operation unit 20 is programmed to allow to arbitrary selection of any dies on the semiconductor wafer as the die to be inspected and the reference die. The operation unit 20 is programmed to permit selection of a die which is not adjacent to any side of a die to be inspected as a reference die. For one example, the any side of die is lateral side and/or longitudinal side of a rectangle die. The die which is not adjacent to any side of die to be inspected is separated from the die to be inspected by at least one intervening die. In following explanation, although the operation unit 20 is explained as it selects the die which is not adjacent to any side of the die to be inspected as a reference die. Of course, at other times the operation unit 20 can also select the adjacent die as the reference die.

Also, the operation unit 20 is programmed to permit setting of an order of dies scanned in sequence so that a die be inspected and a separate reference die are consecutive in the scanning sequence. Furthermore, the operation unit 20 is programmed to permit selection of a die to be inspected and a reference die separated from each other on a semiconductor wafer with at least one die which is intervening in one or two directions of straight outlines of the dies, between the die to be inspected and the reference die.

The processing unit 20 has a computer or other processor which controls the circuit-pattern inspection apparatus built-in. The computer performs a sequence of operations according to executable code embodied in a readable medium when the program installed in the processing unit 20. And the sequence is performed by setting the die to be inspected, the reference die, and the order of dies scanned in consecutive sequence.

Aspects of the methods outlined above may be embodied in software, e.g. in the form of program code executable by the computer or other programmable device. Such software typically is carried on or otherwise embodied in a medium or media. Terms such as "readable medium" used herein refer to any medium that participates in providing instruction and/or data to a programmable processor, such as a CPU for execution or other processing.

On the completion of the specification of an inspection area, the process proceeds to calibration settings for adjusting brightness at the time of the inspection (step 313). The calibration is performed as follows: first obtaining an image, and on the basis of the distribution of its brightness, executing gain adjustment, and brightness correction, of hardware in response to the quantity of signal. In actuality, the calibration is performed by specifying a die where the calibration is performed, and coordinates in the die. The coordinate values, the gain of brightness, and the offset value, which are used for the calibration, are stored as parameters in the process file.

Next, under the various kinds of conditions that have been set up to this time, an image is actually obtained, and thereby image processing conditions for detecting a defect are set (step 314). In the first place, when obtaining the image, a kind of a filter which is used for a detection signal is selected. Then, under the same conditions as those of the inspection, an image of a small area in one chip is actually obtained. Here, on the assumption that for example a scan width of a primary electron beam is 100 μm, the small area indicates an area having a length equivalent to one chip with respect to its width. After obtaining an image, a threshold value used to judge the image to be a defect is inputted, and thereby an image at a position, which has been judged to be a defect, is displayed. Optimum inspection conditions are determined by repeating this. This series of work is called "small-area trial inspection". The parameters including the threshold value and a file, which have been set here, are stored as parameters in the process file. The various kinds of inputs as described above allow the various kinds of parameters required for the inspection to be set.

However, as for a semiconductor wafer that is the substrate to be inspected, there are the unevenness inside a wafer surface and the unevenness caused by the process among production lots. Therefore, the settings of the image processing conditions only for the small-area trial inspection are not sufficient, and accordingly it is necessary to determine the threshold value for the defect judgment taking these unevenness factors into consideration. For this reason, after evaluating the result of the inspection in which the created recipe has been used, the various parameters are written into the classification file and the process file.

To begin with, the final inspection is performed by use of the created recipe file (step 315). In more detail, the final inspection includes the following steps: (1) continuously moving a stage at a constant speed while monitoring its position and the height; (2) scanning a beam with the correcting in real time (followed by the correction of a stage and a Z sensor); (3) detecting a secondary electron, A/D conversion, and inputting an image into a memory; (4) image processing, and comparison for judgment; (5) correcting a beam on a N stripe basis; and (6) displaying the number of the defects and defect positions.

Next, the result is reviewed to check a defect detection level and an improper detection level (step 316). If the conditions are proper, the various kinds of parameters of the recipe, which have been inputted up to this time, are written into the classification file displayed in the classification-file display area 409 and the process file displayed in the process-file display area 410 in FIG. 4 (step 317). Then, by pressing the unload wafer button 407, the substrate to be inspected is unloaded (step 318). After that, the end button 411 is pressed to end the recipe creation mode (step 319).

Here, points which have been improved by the recipe creation mode will be described. As far as the conventional inspection apparatuses are concerned, an operator specifies a die to be inspected only as an area; to be more specific, what can be changed are only directions (for example, X direction, and Y direction) of comparison. The order of comparison checking inside of the specified die cannot be changed at all.

For example, even if comparing between dies at edges in the X direction, or comparing between edges in the Y direction, in a piece of semiconductor wafer, makes it possible to know the unevenness in the semiconductor wafer, the conventional inspection apparatus can compare only adjacent dies. This means that the conventional inspection apparatuses cannot know the unevenness in the semiconductor wafer. Moreover, when manufacturing two or more kinds of semiconductor chips in a piece of semiconductor wafer, comparison checking between different kinds of semiconductor chips is meaningless. Nevertheless, the conventional inspection apparatus performs the comparison checking of only adjacent semiconductor chips in sequence. Therefore, the obtained inspection result will contain useless defect information (false report) that is expected to be wrong in advance and should be eliminated from the inspection result.

For this reason, in this embodiment, an operation screen is provided so that when the operator sets an inspection area, the operator can arbitrarily specify the order of dies to be inspected. As a result, the comparison checking of dies is executed in the specified order.

FIG. 5 is a diagram illustrating a screen for setting the inspection order of dies. In the step 312 of the flowchart shown in FIG. 3, the operator uses the screen shown in FIG. 2 to specify the order of dies to be inspected. In an inspection-area specifying area 110 of the screen shown in FIG. 2, "random" is specified. Then, dies 501 displayed in the map window 87 are clicked in turn as shown in FIG. 5. The specified dies are displayed as their numbers in of the selected order. Moreover, if arrows as shown in FIG. 5 are displayed to indicate the specified order, the order of inspection can be easily known. The inspection is performed by comparing between dies according to this order. In addition, if there is a die to be inserted after the order has been set, insertion processing is allowed. In this case, an insert button 502 shown in a FIG. 5 is first pressed, and a die immediately before the insertion is clicked, and then a die to be inserted is clicked. The die numbers after the inserted die are renumbered in a manner that the die numbers are all incremented by one.

Moreover, if the operator makes a mistake during or after the specification of dies, or if there is a die that need not be inspected, pressing a delete button 503, and then clicking a die to be deleted, will perform deletion processing. As a result, the die numbers after the deleted die are automatically decremented by one.

Thus, if there is a difference in distribution in the semiconductor wafer caused by production (for example, in a case where the inspection result differs when comparing between dies in the circumferential part), it is possible to perform such inspection that only dies in the circumferential part is set and compared at a time. Therefore, it is possible to check whether or not there is a difference in distribution in the semiconductor wafer, and what is more, a die area other than the circumferential part, which does not require inspection, is not inspected. Accordingly, the amount of time is shortened, enabling efficient inspection.

Additionally, in order to prevent the inspection result from including a false report, not specifying dies which should not be compared can avoid misjudgment that recognizes the inspection result as an abnormal condition although it is a false report.

According to one example, the image data of the die to be inspected and the reference die are proceeded to obtain a correlative value with the image processing circuit 82. The control unit 21 classifies the image data based on whether the correlative value is under a predetermined value or not, and the classified data is memorized in the storage means 81. The image data classified as being under the predetermined value indicate a possibility that there is a defect changing gradually ranging from the die to be inspected to reference die. Therefore it is possible to determine whether there is the defect changing gradually between dies based on the classified data.

And according to the other example, in case of the correlative value being low nevertheless it can be determined that there is no specific part defect (ex. a snapping of line pattern, or foreign body) by calculating the difference image signal, there may be a defect changing gradually between dies. Because the correlative value between the images may change by an existence of the specific part defect, there is every possibility that the specific part defect causes a declination of the correlative value. However, in case of the correlative value being low nevertheless it can be determined that there is no specific part defect, it is considered that a difference factor contributes to fall the correlative value. Therefore, it can confirm whether there is the defect changing gradually between dies by judging based on the correlative value between the dies after confirming there is no specific part defect.

Furthermore, the comparing between separate dies can make it possible to confirm a condition of whole semiconductor wafer as a deformation of the semiconductor wafer or a condition of a resist on the semiconductor device. For example, when dies of four corners on the semiconductor wafer are compared in order of left upper, right upper, right lower, left lower, and left upper of the dies from the left upper die as starting point, there may be the deformation in a gap between left and right on the semiconductor device, in case of correlative values between left upper and right upper dies, and between left lower and right lower dies being under predetermined value. The comparing between separate dies can make it possible to do the confirmation of whole semiconductor wafer which can not be accomplished by comparing between adjacent dies.

As discussed above, the inspection result can be obtained selectively by selecting a die for the reference image that is not adjacent to the die to be inspected. As a result, an efficiency of inspection can be improved.

As another example, it is possible to switch techniques of comparison inspection as a need by comparing between separate dies. For example, if a correlative value obtained by comparing between a die on one end of a semiconductor wafer and a die on the other end of the semiconductor wafer is higher than a predetermined value, it can decide that there is no gentle change extending from the one end to the other end. In this case, for example, it is possible to improve the efficiency of inspection by reducing a number of the dies to be inspected. As an example, when the correlative value between the one end and the other end is more than the predetermined value, it may be able to inspect a plurality of dies surrounding the one end of die or the other end of die selectively. When the correlative value is under the predetermined value, it may be appropriate conduct a detailed inspection of all dies on the semiconductor wafer.

As above mentioned, the techniques of comparison inspection are switched by the setting of a die as the reference die that is not adjacent to the die to be inspected and the determining whether the correlative value between the reference die and the die to be inspected is under the predetermined value or not. In this case, it is possible to improve an efficiency of the inspection when the correlative value between the reference die and the die to be inspected is high, and it is possible to maintain an accuracy of inspection when the correlative value is low.

It is also possible to switch from comparing between adjacent dies to comparing between separate dies, when a designed tendency is found in correlative values between the dies is found (luring comparing between adjacent dies.

For example, the setting of the switching of the comparison techniques can be performed by a setting a change from the "ALL OVER IN THE X DIRECTION" to "FIX REFERENCE DIE" and a setting the correlative value on the display as illustrated in FIG. 5 or FIG. 6.

Next, screen operation used when fixing dies to be compared will be described. As described above, as far as the conventional inspection apparatuses are concerned, an operator specifies a die to be inspected only as an area, and accordingly the order of comparison checking inside the specified die cannot be changed at all. In this case, a reference die with which the die to be inspected is compared is an adjacent die, or a die that depends on the order of the stage movement. If there is the moderate distribution of states of produced dies in a semiconductor wafer caused by the process, this embodiment is effective. To be more specific, if a comparison is made between adjacent dies, a slight change is detected, and this change is not recognized as an abnormal condition. However, if it is necessary to detect such an abnormal condition that can be found out by comparing between edges of the semiconductor wafer, or by comparing the circumference with an area around the center, or by comparing the beginning of the inspection with the end of the inspection, this embodiment is effective.

FIG. 6 is a diagram illustrating a screen used for fixed settings of a reference die. In the inspection-area specifying area 110, "Fix reference die" is selected; and in the map window 87 shown in FIG. 2, a reference die 601 which is referred to at the time of comparison is specified. At the time of inspection, the inspection is always performed by comparing with this specified reference die 601.

Besides the reference die 601, a plurality of reference dies can also be specified (reference die 602). For example, as shown in FIG. 6, the reference die 601 is compared with an inspection die row 603; and the reference die 602 is compared with an inspection die row 604.

In this manner, if there is the moderate distribution of abnormal conditions in a semiconductor wafer caused by the production, performing inspection with the reference die being fixed makes it possible to detect the moderate distribution of abnormal conditions in the whole semiconductor wafer. Further, because the die in the semiconductor wafer is always compared with the fixed die, it becomes possible to detect the absolute distribution instead of the relative distribution of abnormal conditions of the die.

Incidentally, devising a method for selecting a fixed die makes it possible to adjust the defect detectivity. To be more specific, by using a die containing many defects as a reference die to be compared, it is possible to reduce as an offset the total number of defects in the semiconductor wafer. As a result, an uncritical defect is not detected, which reduces the number of target defects to be reviewed after the inspection, making it possible to improve the efficiency in review.

Moreover, even if two or more kinds of semiconductor chips are provided on one semiconductor wafer, it is possible to inspect only required chips, which enables efficient inspection.

Such settings of targets to be inspected can be applied not only to the SEM image in this embodiment but also to an image of an optical microscope and an image obtained with a laser beam in the same way of thinking.

As described above, because the operator can quickly perform the inspection of a chip, the sampling inspection of a wafer, and the like, while viewing the screen, it is possible to quickly detect a defect across the whole product or a defect in a specific area. Furthermore, because fluctuations of process conditions are reliably detected, the fluctuation can be fed back to the process and also to the adjustment of the difference in man-hour and of an expenditure budget.

If the above-discussed inspection apparatus is applied to a substrate product process, it possible to detect an abnormal condition relating to a product, an apparatus, or conditions at an early stage and with a high degree of accuracy by referring to a screen. Accordingly, it is possible to quickly take measures against the abnormal condition during the substrate manufacture process. As a result, the defective rate of a semiconductor device and of other substrates can be reduced, enabling an improvement in productivity.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A circuit-pattern inspection apparatus comprising:
a beam source,
a detector for detecting signals obtained from beam irradiation of a part of a specimen,
a memory for storing the signals as an image,
an operation unit for selecting inspection dies in one or more inspection die rows to be scanned and setting fixed separate reference dies to be compared with the inspection dies of the inspection die rows, and
a processing unit for comparing images of first die of one of the inspection die rows stored in the memory with a first reference image of a first fixed reference die of said fixed separate reference dies stored in the memory, comparing images of second die of another of the inspection die rows stored in the memory with a second reference image of a second fixed reference die of said fixed separate reference dies stored in the memory, and for identifying a defect on at least one of the dies of said inspection die rows.

2. A circuit-pattern inspection apparatus comprising:
a beam source,
a detector for detecting signals obtained from beam irradiation of a part of a specimen,
a memory for storing the signals as an image,
an operation unit, for selecting inspection dies in an inspection die row to be scanned, and
a processing unit for comparing two images of at least three images of dies of which two images of dies are selected in said inspection die row and the other image is an image of a fixed separate reference die, and for identifying defects on the die of the inspection die row.

3. A circuit-pattern inspection apparatus comprising:
a beam source;
a detector for detecting signals obtained from beam irradiation of a part of a specimen;
a memory for storing the signals as one or more images;
an operation unit for arbitrarily selecting inspection dies to be inspected in a sequence and at least one fixed reference die and storing images of the of dies in memory, and
a processing unit for comparing images from the memory for a plurality of the dies to be inspected to one or more images from the memory for the at least one fixed reference die, and for detecting defects on the plurality of dies to be inspected based on a result of the comparison.

* * * * *